United States Patent [19]

Williams et al.

[11] 4,140,830

[45] Feb. 20, 1979

[54] POLYMER COMPOSITE ARTICLES CONTAINING EPISULFIDE SUBSTITUTED ORGANOSILICON COUPLING AGENTS

[75] Inventors: Thomas C. Williams, Ridgefield, Conn.; George E. Totten, Hartsdale, N.Y.

[73] Assignee: Union Carbide Corporation, New York, N.Y.

[21] Appl. No.: 810,968

[22] Filed: Jun. 28, 1977

[51] Int. Cl.$^2$ ................. B32B 17/04; B32B 19/02; B32B 25/08

[52] U.S. Cl. .................... 428/251; 428/403; 428/405; 428/406; 428/407; 428/417; 428/412; 428/421; 428/429; 428/447; 428/450; 428/454; 428/457; 428/474; 428/480; 428/492; 428/500; 260/448.2 N; 260/448.8 R

[58] Field of Search ............... 428/251, 417, 429, 412, 428/421, 443, 447, 450, 454, 457, 474, 480, 492, 500; 260/448.2 A, 448.8 R

[56] References Cited

U.S. PATENT DOCUMENTS

| | | | |
|---|---|---|---|
| 3,706,592 | 12/1972 | Thomson | 428/429 X |
| 3,717,617 | 2/1973 | Marrs et al. | 428/450 X |
| 3,768,537 | 10/1973 | Hess et al. | 152/330 |

*Primary Examiner*—P. C. Ives
*Attorney, Agent, or Firm*—Reynold J. Finnegan

[57] ABSTRACT

Polymer composites, such as rubber, thermoset and thermoplastic articles, comprising the reaction product of (a) an organic polymer, (b) an inorganic substrate and (c) an episulfide substituted organosilicon coupling agent, and articles comprising an inorganic substrate treated with an episulfide substituted organosilicon coupling agent.

5 Claims, No Drawings

POLYMER COMPOSITE ARTICLES CONTAINING EPISULFIDE SUBSTITUTED ORGANOSILICON COUPLING AGENTS

BACKGROUND OF THE INVENTION

This invention relates to novel polymer composite articles of manufacture comprising the reaction product of (a) an organic polymer, (b) an inorganic substrate and (c) an episulfide substituted organosilicon coupling agent, as well as to articles of manufacture comprising an inorganic substrate treated with anepisulfide substituted organosilicon coupling agent.

The use of various silicon coupling agents to enhance the adhesion of various inorganic substrates with a broad variety or organic polymers to promote coupling and bonding therewith is well known in the art. Note for example, U.S. Pat. Nos. 2,832,754; 2,971,864; 3,258,477; 3,661,628; 3,671,562; 3,705,911; 3,706,592 and 3,754,971; and the like. Thus, as is conventionally understood in the art the silicon coupling agent serves as a crosslinker that is chemically or physically bonded to both the inorganic substrate and the organic polymer in the polymer composite.

SUMMARY OF THE INVENTION

Accordingly, it is an object of this invention to provide polymer composite articles of manufacture comprising the reaction product of (a) an organic polymer, (b) an inorganic substrate and (c) a novel episulfide substituted organoslilcon composition of matter as disclosed in the concurrently filed U.S. Application No. 810,851 now abandoned It is another object of this invention to provide articles of manufacture comprising an inorganic substrate treated with said novel episulfide substituted organosilicon compositions of matter. Other objects and advantages of this invention will become readily apparent from the following description and appended claims.

More specifically then, one embodiment of this invention relates to a polymer composite article of manufacture comprising the reaction product of (a) an organic polymer, (b) an inorganic substrate, and (c) an episulfide substituted organoslilcon coupling agent selected from the class consisting of (i) episulfide substituted organosilane compounds having the formulat

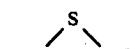

$$X_{4-(a+b)}-\underset{R'_b}{Si}[(R)_n(Q)_t(Y)]_a \qquad (I)$$

wherein R' is a monovalent radical selected from the class consisting of hydrogen, hydrocarbon radicals and substituted hydrocarbon radicals;

wherein X is a hydrolyzable radical selected from the class consisting of alkoxy, aryloxy, acyloxy, secondary amino and aminooxy radicals;

wherein R is a divalent bridging group selected from the class consisting of hydrocarbon radicals, groups of the formula —R"OR"— and groups of the formula —R"SR" —wherein R" is a divalent hydrocarbon radical;

wherein Q is an oxygen atom or a sulfur atoms;

wherein Y is an episulfide radical selected from the class consisting of

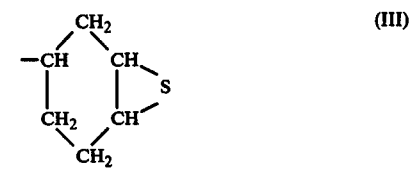

wherein $n$ has a value of 0 or 1 and $t$ has a value of 0 or 1, with the proviso that when $n$ is 0, then $t$ is 0 and $Y$ is an episulfide radical of formula (II) above; and wherein $a$ has a value of 1 to 3 and $b$ has a value of 0 to 2, with the provisor that the sum of (a+b) is not greater than 3; (ii) episulfide substituted organosiloxanes consisting essentially of siloxy units having the formula:

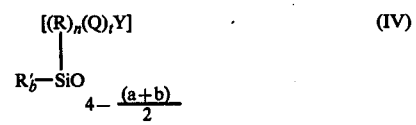

$$\underset{R'_b-SiO_{\frac{4-(a+b)}{2}}}{[(R)_n(Q)_tY]} \qquad (IV)$$

wherein R', R, Q, Y, $n$, $t$, $a$ and $b$ are the same as defined above; and (iii) episulfide substituted organosiloxane copolymers consisting essentially of at least one siloxy unit represented by formula (IV) above and at least one siloxy unit represented by the formula

$$R'_c-SiO_{\frac{4-c}{2}} \qquad (V)$$

wherein R' is the same as defined in formula (IV) above and wherein $c$ has a value of from 0 to 3 inclusive.

DESCRIPTION OF THE PREFERRED EMBODIMENTS

The polymer composite articles of manufacture of this invention can correspond to any heretofore conventional polymer composite comprising an organic polymer bonded to an inorganic substrate through the use of conventional silicon coupling agents, the difference being that the polymer composite articles of manufacture of this invention employ as the coupling agent, the above referred to episulfide substituted organosilicon compositions of matter. Thus, the polymer composite articles of manufacture of this invention include such conventional articles as rubber, thermoplastic and thermosetting resins, paints, varnishes, inks and the like.

The organic polymer components of the novel composites of this invention as well as methods for their preparation are well known in the art and include a wide variety of polymers. Illustrative examples of such polymers, either singularly or in adjuncture with each other include any of the homopolymers and copolymers of olefinic and diolefinic monomers such as ethylene, propylene, butylenes, methylpentenes, styrene ring substituted styrenes, alphamethyl styrene, vinyl chloride, vinyl fluoride, vinylidene chloride, acrylonitrile, methacrylonitrile, vinyl alcohol esters, acrylic acid and its esters and amides, methacrylic acid and its esters and amides, allyl phthalate esters, butadiene, isoprene, chloroprene, ethylidene norbornene, 1,5-hexadiene, divinyl benzenes and the like, as well as synthetic condensation polymers commonly classed as alkyd resins, polyesters, nylons, phenolics, epoxides polysulfones, polysulfonamides, polysulfides, polyurethanes, polyureas and the like, as well as oligomers and polymers derived from plant and animal sources such as cellulose esters and ethers, carbon-carbon unsaturated fatty acid triglycerides and natural hevea and ficus rubbers and the like.

The more preferred organic polymers employable in this invention are the conventional thermoplastic forming resins, thermoset forming resins, and rubber forming polymers. Illustrative of some of the more preferred thermoplastic forming resins include, e.g. polyethylene, polypropylene, polystyrene, polyvinylchloride, polyvinyl butyral, nylon, polyacrylonitrile, polycarbonates, polyesters, and the like as well as copolymers and terpolymers thereof. Illustrative of some of the more preferred thermoset forming resins include, e.g. unsaturated polyesters, epoxies, phenolics, melamine, and the like.

The more preferred organic polymers employable in this invention are the conventional vulcanizable unsaturated rubber polymers used to prepare vulcanizable rubber compounds. Illustrative of such vulcanizable rubber polymers are natural rubber and synthetic rubber polymers as disclosed, e.g. in The Elastomer Manual (1972 Edition) published by International Institute of Synthetic Rubber Producer, Inc., such as styrenebutadiene rubber polymers, butadiene rubber polymers, ethylene-propylene rubber terpolymers, chloroprene rubber polymers, nitrile rubber polymers, bromo- and chlorobutyl rubber polymers polyisoprene rubber polymers, and the like. Especially preferred are the conventional sulfur vulcanizable rubber polymers such as natural rubber, styrenebutadiene rubber polymers, butadiene rubber polymers, and polyisoprene rubber polymers.

The inorganic substrates employable in this invention are well known in the art and include any conventional inorganic substrate generally employed in rubber, thermoplastic and thermosetting resins, paints varnishes, inks and the like, and which are substantially reactive toward the episulfide substituted organosilicon coupling agents employed in this invention. Illustrative examples of such inorganic substrates include such reinforcing materials, pigments or fillers such as siliceous materials such as plate glass, glass fibers, asbestos, sand, clay, talc, silica, e.g. hydrated silica, precipitated silica, fumed silica, silica aerogels and silica xero-gels, metal silicates, e.g. aluminum silicate, calcium silicate, calcium metasilicate, magnesium silicate, feldspar, concrete, ceramic materials and the like; metals such as aluminum, copper, cadmium, chromium, magnesium, nickel, silver, tin, titanium, zinc, and the like; the alloys of such metals as brass, bronze, steel, and the like including metals which have been surface treated with phosphates, chromates, and the like; metal oxides such as aluminum oxide, iron oxides, lead oxides, titanium dioxide, zinc oxide and the like. Of course, it is understood that the particular configuration of the inorganic substrate employed is not critical and that the inorganic materials can be in any various form such as sheets, plates, blocks, wires, cloth, fibers, filaments, particles, powders and the like. The preferred inorganic substrates are the siliceous materials, especially silica and metal silicate fillers or pigments.

The episulfide substituted organosilicon compositions of matter employable in this invention are those episulfide substituted organosilanes and organosiloxanes disclosed in said concurrently filed U.S. application Ser. No. 810,851 the disclosure of which is encompassed herein by reference thereto.

More specifically such episulfide substituted organosilicon compositions of matter include episulfide substituted organolsilane compounds having the formula:

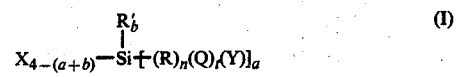

wherein X, R, R', Q, Y, $a$, $b$, $n$ and $t$ are the same as defined above.

Illustrative radicals represented by R' in formula (I) above are hydrogen and monovalent hydrocarbon radicals which can contain from 1 to 20 carbon atoms, and which are unsubstituted or substituted with substituents which are inert under the reaction conditions employed in preparing the silane compounds. Such hydrocarbon radicals include straight and branched chain alkyl radicals (e.g. methyl, ethyl, n-propyl, isopropyl, n-butyl, isobutyl, t-butyl, n-pentyl, n-hexyl, 2-ethylhexyl, n-decyl, n-dodecyl, n-tetradecyl, n-hexadecyl, n-octadecyl, eicosyl and the like); alkenyl radicals (e.g. vinyl, allyl, 2,4-hexadienyl, 9, 12, 15-octadecatrienyl, and the like); cycloalkyl radicals (e.g. cyclopentyl, cyclohexyl, and the like); aryl radicals (e.g. phenyl, naphthyl, biphenyl and the like); cycloalkenyl radicals (e.g. 3-cyclohexenyl and the like); aralkyl radicals (e.g. p-methylphenyl, p-cyclohexylphenyl, alphamethylnaphthyl, and the like); haloaryl radicals (e.g. 4-chlorophenyl 2, 4-dichlorophenyl, chloronaphthyl, and the like); nitro aryl radicals (e.g. 4-nitrophenyl, and the like); cyanoalkyl radicals (e.g. beta-cyanoethyl, gamma-cyanopropyl, and the like). Of course, it is understood that such R' radicals can be the same or different in any given silane compound. Preferably R' is hydrogen or a monovalent unsubstituted hydrocarbon radical. More preferably R' is an alkyl radical containing from 1 to 18 carbon atoms and most preferably from 1 to 8 carbon atoms.

Illustrative hydrolyzable radicals represented by X in formula (I) above include alkoxy radicals (e.g. methoxy, ethoxy, propoxy, isopropoxy, 2-methoxyethoxy, dodecyloxy, betacyanoethoxy, and the like); aryloxy radicals (e.g. phenoxy, and the like); acyloxy radicals (e.g. formyloxy, acetoxy, and the like); secondary amino radicals such as dialkylamino (e.g. dimethylamino, diethylamino and the like) and aminooxy radicals such as dialkylaminooxy (e.g. diethylaminooxy and the like); Of course, it is understood that each X radical can be the same or different in any given silane compound, although normally it is preferred that each X be the same. Preferably X is an alkoxy radical, especially alkoxy radicals selected from the group consisting of methoxy, ethoxy, and 2-methoxyethoxy.

Illustrative divalent bridging radicals represented by R in formula (I) above include hydrocarbon radicals, oxygen containing hydrocarbon radicals (i.e. —R'λ'OR"—) and sulfur containing hydrocarbon radicals (i.e. —R"SR"—). Normally, such radicals contain from 1 to 12 carbon atoms. Illustrative divalent hydrocarbon radicals represented by R include alkylene radicals (e.g. methylene (—CH$_2$—) ethylene, propylene, isopropylene, butylene, neopentylene, pentylene, 2-ethylhexylene, dodecylene and the like); arylene radicals (e.g. phenylene, and the like); arylene containing alkylene radicals (e.g. methylenephenylene —(CH$_2$C$_6$H$_4$—), and the like); and the like. The oxygen containing hydrocarbon radicals represented by R are those of the formula —R"OR"—, wherein R" is a divalent hydrocarbon radical, such as alkyleneoxyalkylene radicals (e.g. ethyleneoxymethylene ($-C_2H_4OCH_2-$), propyleneoxymethylene, ($-C_3H_6OC_2H_4-$), propyleneoxypropylene ($-C_3H_6OC_3H_6-$) and the like); aryleneoxyalkylene radicals (e.g. phenyleneoxymethylene ($-C_6H_4OCH_2-$), and the like); and the like. The sulfur (or thio) containing hydrocarbon radicals represented by R are those of the formula —R"SR"— wherein R" is a divalent hydrocarbon radical such as alkylenethioalkylene radicals (e.g. ethylenethiomethylene ($-C_2H_4SCH_2-$), propylenethiomethylene ($-CH_2CH_2CH_2SCH_2-$), propylenethioethylene ($-C_3H_6SC_2H_4-$), propylenethiopropylene ($-C_3H_6SC_3H_6-$) and the like); arylenethioalkylene radicals (e.g. phenylenethiomethylene ($-C_6H_4SCH_2-$), and the like); and the like. Preferably R is an alkyleneoxyalkylene radical wherein each divalent alkylene radical contains from 1 to 3 carbon atoms, the most preferred R bridging group being propyleneoxymethylene ($-CH_2CH_2CH_2OCH_2-$).

As pointed out above, when $n$ has a value of O, then $t$ has a value of O and Y must be an episulfide radical of formula (II) above (i.e. the episulfide radical of formula (II) is directly bonded to the silicon atom through its free valuent carbon atom). Thus, when $n$ has a value of 1, then $t$ can have a value of 0 or 1 and Y can be an episulfide radical of either formula (II) above or formula (III) above, which episulfide radicals are bonded to R either directly when $t$ is 0 or through an oxygen atom or sulfur atom of Q when $t$ is 1. Moreover, the preferred episulfide substituted organosilanes of formula (I) above are those wherein $a$ has a value of 1, $b$ has a value of 0 and $n$ has a value of 1.

Accordingly, the more preferred episulfide substituted organosilane compounds employable in this invention are those having the formula $$X_3Si-(R)-Y$$

wherein X is a hydrolyzable radical as defined above, especially an alkoxy radical such as methoxy, wherein R is a divalent alkylene or alkyleneoxyalkylene bridging radical as defined above, especially an alkyleneoxyalkylene radical such as propyleneoxymethylene, and wherein Y is an episulfide radical as defined above, especially

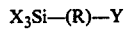

The episulfide substituted organosilanes employable in this invention can be prepared in any number of ways as described in said concurrently filed U.S. application Ser. No. 810,851.

Preferably the episulfide substituted organosilanes are prepared by reacting a corresponding epoxide containing silane with thiourea as shown by the following equation

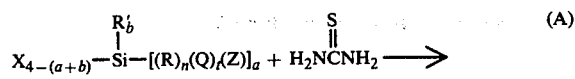

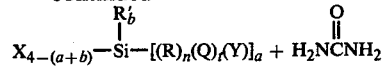

wherein X, R', R, Q, Y, $a$, $b$, $n$ and $t$ are the same as defined above and wherein Z is a epoxide radical selected from the class consisting of

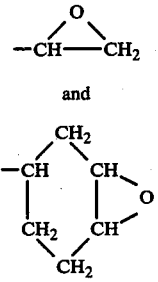

More specifically said process can be illustrated as follows:

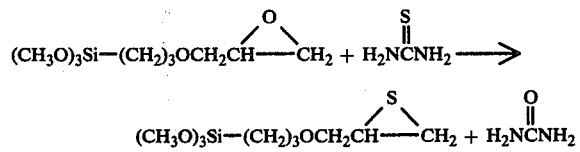

Alternatively the episulfide substituted organosilanes used in this invention can also be prepared by reacting a corresponding epoxide containing silane with a metal thiocyanate salt as shown by the following equation:

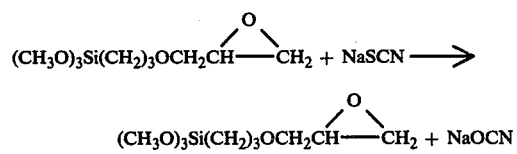

wherein X, R', R, Q, Z, Y, $a$, $b$, $n$ and $t$ are the same as defined above and M is a metal such as an alkali metal. More specifically said process may be illustrated as follows:

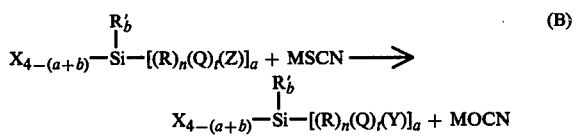

As seen by the above equations the oxygen atom of the epoxide radical, Z, of the starting material is replaced by the sulfur atom of the thiourea or metal thiocyanate salt to form the desired episulfide radical, Y, thus resulting in the desired corresponding episulfide substituted organosilane products.

The reaction compounds, i.e. epoxide containing silanes, thiourea, or matal thiocyanate salts, and/or methods for their production, which can be used in the above described processes (A) and (B) are well known in the art. Illustrative epoxide containing silanes include gamma-glycidoxyproxyltrimethoxysilane, beta-(3,4-epoxycyclohexyl)-ethyltrimethoxysilane, and the like. Illustrative metal thiocyanate salt starting materials include, e.g. the alkali metal thiocyanates such as NaSCN, KSCN, and the like.

The process factors involved in forming the episulfide substituted organosilanes by either of the above two described preferred methods (A) and (B) are not critical although certain practical choices may be made as described below.

As pointed out above, the two methods of preparation merely involve reacting a corresponding epoxide containing silane with thiourea (Process (A)) or a metal cyanate salt (Process (B)) and maintaining the reaction until the oxygen atom of the epoxide starting material has been replaced with the sulfur atom of the thiourea or metal thiocyanate salt to form the desired episulfide substituted organosilane.

No special catalysts are needed for either process. It is advantageous, however, to employ a polar solvent. Suitable solvents include aliphatic alcohols such as methanol, ethanol, n-propanol, t-butanol, and the like, and aliphatic ethers such as terahydrofuran and the like. The amount of solvent used is not narrowly critical, the solvent normally being employed in an amount sufficient to dissolve the reactants involved, although lower or higher amounts can be employed if desired. Of course, it is to be understood that the solvent employed should be chosen so as to not adversely react with the hydrolyzable groups on the starting silane or otherwise adversely affect the desired reaction.

In general, both processes (A) and (B) described above merely involve mixing both reactants and the solvent and maintaining the resultant solubilized mixture at the reaction temperature until the reaction has been completed. Any convenient order of mixing can be employed. In both processes stoichiometric amounts of reactants can be used, while it may sometimes be advantageous to use an excess of urea or metal thiocyanate in order to increase the yield or the reaction rate. Both processes are generally conducted at atmospheric pressure, although subatmospheric or superatmospheric pressures may be used if desired. It is also preferred that said processes (A) and (B) be initially conducted in a substantially anhydrous environment due to the reactivity of the reactants and products towards water, thus both processes are normally carried out under a dry nitrogen atmosphere.

The reaction temperature for both processes (A) and (B) are not narrowly critical and can range from about room temperature up to and including the reflux temperature of the reaction mixture as may be convenient for the operator, the most preferred reaction temperature for any specific reaction being obviously easily determinable by routine experimentation. Both processes (A) and (B) are generally completed within from about one to about four hours but may be completed faster or take longer depending on such obvious factors as the amounts and types of reactants involved, and the solvent and reaction temperature employed. Completion of said reactions is easily determinable e.g. by the cessation of any further formation of solid urea of cyanate salt by-product. The solvent employed and the by-product of said preferred processes (A) and (B) can be easily removed, and the desired normally liquid episulfide substituted silane products recovered by any suitable conventional method. For example, the solvent can be removed by distillation and the solid by-products by filtration, centrifuging and the like. The episulfide substituted organosilanes can be advantageously employed in their crude product form or, if desired, undergo conventional treatment procedures in order to obtain a purer product prior to use.

Illustrative episulfide substituted organosilanes obtained from their corresponding epoxide silane starting materials include

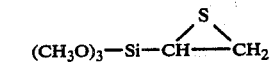

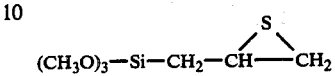

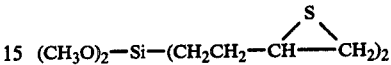

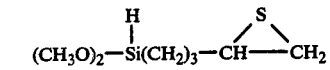

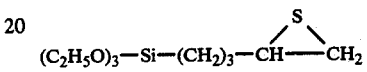

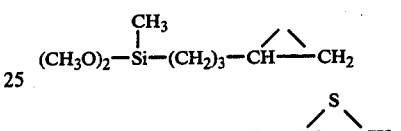

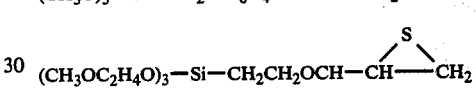

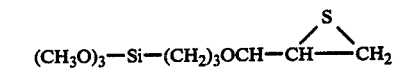

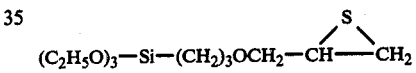

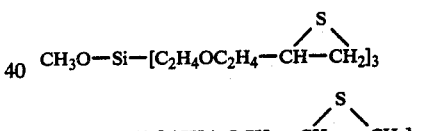

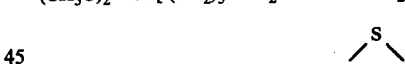

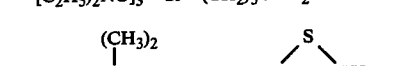

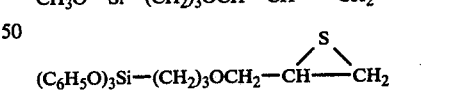

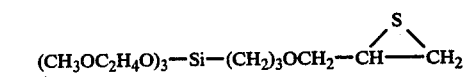

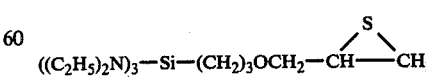

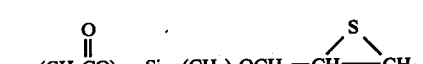

-continued

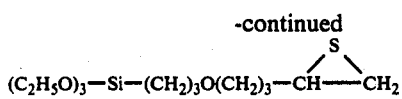

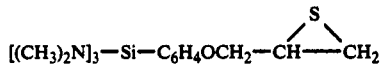

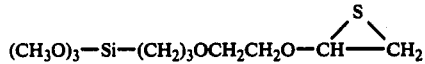

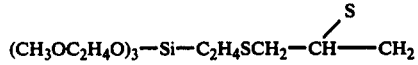

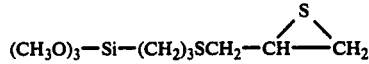

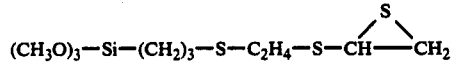

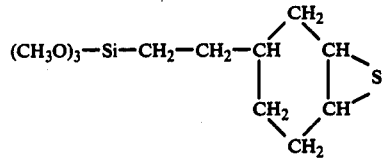

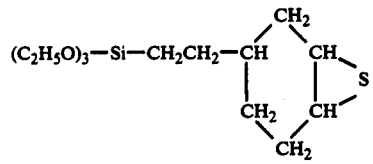

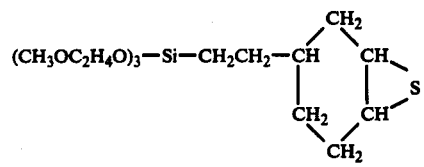

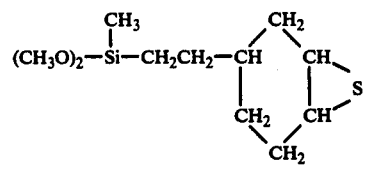

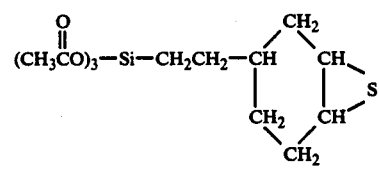

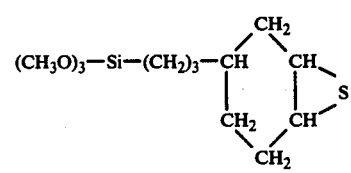

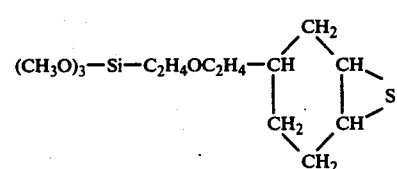

-continued

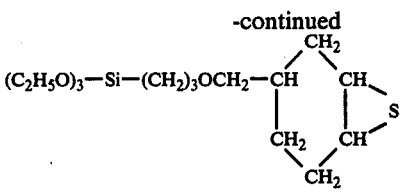

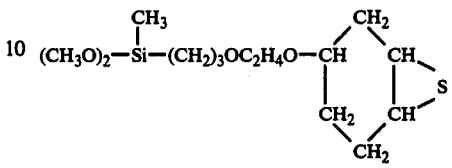

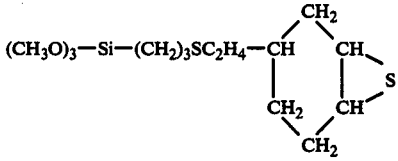

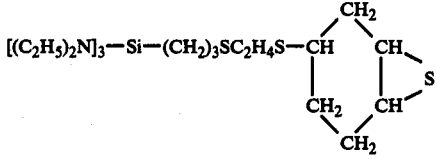

and the like, the most preferred episulfide substituted organosilane being 1,2-epithio-4-oxa-7-trimethoxysilyl heptane.

Alternatively the episulfide substituted organosilicon coupling agent compositions of matter employable in this invention include episulfide substituted organosiloxanes Illustrative of such episulfide substituted organosiloxanes are those consisting essentially of siloxy units having the formula

wherein R', R, Q, Y, $n$, $t$, $a$ and $b$ are the same as defined in formula (I) above; as well as episulfide substituted organosiloxane copolymers consisting essentially of at least one siloxy unit represented by formula (IV) above and at least one siloxy unit represented by the formula

wherein R' is the same as defined in formula (IV) above and wherein $c$ has a value of from 0 to 3 inclusive.

For example, the above discussed episulfide substituted organosilanes can be hydrolyzed and condensed in the conventional manner, either alone or together with other hydrolyzable silanes to produce siloxanes consisting essentially of the siloxy units of formula (IV) above or copolymer siloxanes consisting essentially of siloxy units of formula (IV) above and formula (V) above. When the episulfide substituted organosilanes of this invention are cohydrolyzed and condensed with other conventional hydrolyzable silanes, the siloxanes produced are copolymers consisting essentially of siloxy units of formula (IV) above and formula (V) above. Illustrative conventional hydrolyzable silanes are those of the formula $R'_c—Si—X_{4-c}$ wherein $R'$ and $c$ are the same as defined above and X is a hydrolyzable group such as an alkoxy radical, e.g. methoxy.

Thus, in general, the episulfide substituted organosiloxane must contain at least one siloxy unit such as $$[Y(Q)_t(R)_n]Si(R')O, \quad [Y(Q)_t(R)_n]Si(R')_2O_{0.5},$$

$$[Y(Q)_t(R)_n]SiO_{1.5}, \quad [Y(Q)_t(R)_n]_2SiO,$$

$$[Y(Q)_t(R)_n]_3SiO_{0.5} \text{ or } [Y(Q)_t(R)_n]_2Si(R')O_{0.5}$$

and may contain one or more siloxy units, such as $R'_3SiO_{0.5}$, $R'_2SiO$, $R'SiO_{1.5}$, or $SiO_2$; wherein Y, Q, R, R', $t$ and $n$ are the same as defined above. Of course, it is understood that the siloxanes can contain a minor amount of hydrolyzable groups if complete hydrolysis is not obtained.

The hydrolysis and condensation of the episulfide substituted organosilanes is not critical and can be carried out in any conventional manner, and such procedures are well known in the art. Alternatively, the episulfide substituted organolsiloxanes can be prepared by reacting a corresponding epoxide containing siloxane with thiourea or a metal thiocyanate salt in the same manner as described above for producing the episulfide substituted organosilanes. However, it is to be understood that when such an alternative method is employed that the siloxanes can also contain hydrolyzable end-blocked siloxy units if the starting materials contain same, and in those instances wherein less than the equivalent amount of thiourea or metal thiocyanate are employed, the siloxanes can also contain siloxy units having unreacted epoxide groups;

The function of a silicon coupling agent to provide a strong chemical bridge between the inorganic substrate and the organic polymer employed is well known in the art. It is of course understood that for effective coupling action in a particular polymer substrate composite, it is necessary to select the appropriate coupling agent, i.e. one which is suitably reactive towards both the polymer component and the substrate component for each particular polymer-substrate composite considered. Thus, while there may be more than one appropriate coupling agent for a particular polymer-substrate composite, a given coupling agent may not be appropriate for all polymer composites. However, the selection of the most preferred coupling agent for any particular polymer composite is well within routine experimentation.

The particular manner of compounding the polymer composite articles of manufacture of this invention as well as the various amounts of ingredients employed are not critical and merely depend on the particular finished polymer composite desired along with the ultimate end use for which it is to be employed and such steps as compounding, heating, crosslinking or vulcanizing, and the like may be conducted in any conventional manner heretofore employed in preparing conventional polymer composites such as thermoplastic resin composites, thermoset resin composites, vulcanized rubber composites, and the like.

For example, in the case of conventional polymer-filler type composites such as vulcanized rubber articles, the episulfide substituted organosilicon coupling agents and/or solubilized solutions thereof can be added to the vulcanizable rubber polymer batch together with the substrate filler and various other additives during mill or banbury mixing. Alternatively the substrate fillers or vulcanizable rubber polymers can be treated (coated) with the episulfide substituted organosilicon coupling agents and/or solubilized solutions thereof prior to incorporation into the rubber polymer or filler master batch. Generally, it is preferred to employ the episulfide substituted organosilicon coupling agents neat, mix them with the substrate filler, preferably a silica or metal silicate filler, and add the mixture to the polymer batch prior to the incorporation of the other conventional additives normally employed in such polymer-filled composites. Moreover, if desired, the episulfide substituted organosilicon coupling agents can be taken up (adsorbed) on any suitable conventional microporous carrier, e.g. Microcel E, a calcium silicate, prior to use to form a dry free flowing powder concentrate. Such microporous carriers, in the amounts normally used, do not affect the properties of the composite product articles and the free flowing powder concentrate provides convenience in handling and metering of the coupling agent. As pointed out above, the particular procedures involved and amount ratios of the components employed are all within the knowledge of one skilled in the art and are left to the choice of the operator. More specifically, however, the preferred polymer composite articles of this invention are vulcanized rubber articles. Thus, in general the amount of episulfide substituted organosilicon coupling agent employed in the vulcanized rubber composites of this invention will normally range from about 0.1 to about 20 parts by weight (preferably from about 0.2 to about 10 parts by weight) per 100 parts by weight of inorganic substrate filler employed although higher or lower amounts may be employed if desired. Of course, the amount of inorganic substrate filler employed merely depends on the desired rubber product end use and may range from about 5 up to as high as 300 parts by weight or higher per 100 parts by weight of vulcanizable rubber polymer employed. The vulcanizable rubber compound is normally vulcanized in the presence of conventional sulfur or peroxide curatives that are well known in the art. For example, a conventional sulfur curative may include per 100 parts by weight of vulcanizable rubber polymer from about 0.5 to 4 parts by weight of sulfur, about 2 to 5 parts by weight of zinc oxide, and about 0.2 to 3 parts by weight of accelerators (e.g. diphenylguanidine), while a conventional peroxide curative generally may include per 100 parts by weight of vulcanizable rubber polymer from about 1 to about 8 parts by weight of an organic peroxide e.g. dicumyl peroxide, $\alpha$, $\alpha'$-bis(t-butyl peroxy) diisopropylbenzene, and the like. The vulcanizable procedure of a rubber polymer is well known in the art and in general may be conducted at temperatures ranging from 260° F. to about 360° F., although lower or higher temperatures may be employed if desired. Of course, it is obvious that if desired the vulcanizable rubber composites of this invention may contain any of the conventionally additional ingredients such as extenders, carbon blacks, processing oils, plasticizers, antioxidants, lubricants, accelerators, retardants, coloring pigments, and dyestuffs, and the like, normally employed in conventional vulcanized rubber composites and such is well within the knowledge of one skilled in the art.

In the case of conventional rubber, thermoplastic or thermoset polymer laminate type composites wherein e.g. the inorganic substrate is glass fibers, it is generally preferred to pretreat (coat) the inorganic substrate with the episulfide substituted organosilicon coupling agent prior to bonding with the organic polymer employed although the coupling agent and organic polymer can be deposited together on the substrate and then bonded or the polymer first treated with the coupling agent and then coated onto the substrate and bonded, if desired. The episulfide substituted organosilicon coupling agent may be employed neat, although it is generally preferred to employ a solubilized solution of the coupling agent by employing an appropriate solvent such as those discussed above, and more preferably to employ an aqueous composition of the episulfide substituted organosilicon coupling agent, especially the silane coupling agents. The production of such polymer laminate type composites is well known in the art. The various amounts of compounds employed of course merely depend upon the episulfide substituted organosilicon coupling agent employed, the surface are to be covered, the organic polymer to be bonded to the substrate and the like. Moreover, the method of coating the substrate is not critical and the coupling agent can be sprayed, brushed, poured, or rolled on to the surface of the substrate and the like, or alternatively the substrate can be dipped into a solvent solution or aqueous composition of the coupling agent. Likewise the temperature at which the bonding reaction is carried out can be varied over a wide range depending upon the specific compounds employed. In general, heat temperatures will normally be in the range of about 100° C. to about 350° C. or higher, although if desired the bonding between the substrate coupling agent and organic polymer may also be carried out by the use of ultra-violet radiation, X-rays and the like. Of course, it is obvious that such polymer laminate type composites if desired may contain any of the conventional additional ingredients normally employed in conventional polymer-laminate articles such as catalysts, antioxidants, pigments, and the like.

Accordingly, another aspect of this invention is directed to an inorganic substrate as defined above treated with an episulfide substituted organosilicon coupling agent as defined above. When employed aqueous compositions of the coupling agent generally comprise from about 0.1 to about 20 parts by weight of an episulfide substituted organosilicon coupling agent and from about 99.9 to about 80 parts by weight of water. Such aqueous compositions may be in the form of solutions, dispersions or emulsions and may be especially suitable for use as sizing and finishing agents in the glass fiber industry. If desired, the episulfide substituted organosilicon coupling agent can be employed in the form of a water-soluble solvent solubilized solution. Generally, it is preferred to employ aqueous compositions of an episulfide substituted organosilane coupling agent. Of course, it is to be understood that since the episulfide substituted organosilicon coupling agents contain hydrolyzable groups (e.g. alkoxy radicals) the aqueous compositions of such include and encompass the hydrolyzates, partial hydrolyzates, condensates and partial condensates of said silicon coupling agents. The treatment or coating of the inorganic substrate with said aqueous compositions is conventional as discussed above.

Thus, it will be readily apparent to those skilled in the art that the episulfide substituted organosilicon coupling agents employed in this invention lend themselves to any conventional process where organic polymers are to be bonded to inorganic substrates and thus to the formation of a wide range of polymer composite articles of manufacture such as filled vulcanized rubber products, filled thermoset and thermoplastic products, organic polymer-substrate (e.g. glass fibers) laminate products, and the like, heretofore prepared with conventional silane coupling agents.

Evidence of action by a coupling agent is manifested through changes in composite properties away from the values displayed in the absence of the agent and the properties which may be favorably altered are many and varied. In elastomeric and resinous composites, the improved effects attributable to the instant invention are often seen in terms of its increased resistance to deforming forces and abrasion resistance and in decreased hysteresis losses in flexure. For example, the reactivity and/or bonding between the organic polymer, inorganic substrate and episulfide substituted organosilicon coupling agent of this invention is demonstrated by the improved physical properties in the finished polymer composite product, such as tensile modulus, and the like as compared to the physical properties of the same finished composite product prepared without the use of the episulfide substituted organosilicon coupling agent. Likewise, while the episulfide substituted organosilicon "coating" per se on the pretreated inorganic substrate articles of this invention is not measurable, its presence is also confirmed by such improved physical properties in the finished polymer composite prepared with such pretreated substrates as compared to the same finished product prepared with an untreated substrate and without the use of any episulfide substituted organosilicon coupling agent.

It has been further surprisingly discovered that such physical properties of the finished polymer composite products of this invention can in general be improved even further when an organic primary or secondary amine is employed along with the episulfide substituted organosilicon coupling agents of this invention.

Accordingly, another aspect of this invention relates to polymer composites containing an accelerator for said coupling agent. Likewise this invention relates to articles of manufacture comprising an inorganic substrate treated with an episulfide substituted organosilicon coupling agent, as discussed above, said treatment having taken place in the presence of an organic primary or secondary amine accelerator for said coupling agent.

The use of organic primary and secondary amines have in general been found to accelerate or enhance the coupling action of the episulifide substituted organosilicon coupling agents as demonstrated by an even further general improvement in the physical properties of the finished articles of manufacture, such as tensile modulus, and the like, as compared to the physical properties of the same finished articles prepared in the absence of such an organic primary or secondary amine accelerator for the coupling agent.

Illustrative organic primary and secondary amine compounds that may be employed as accelerators for the episulfide substituted organosilicon coupling agents in the preparation of the articles of manufacture of this invention include such compounds as ethylamine, dimethylamine, diethylamine, di-n-butylamine, sec-butylamine, n-octylamine, 2-hydroxyethylamine, bis-(2-hydroxyethyl)amine, 2-methoxyethylamine, 3-hydroxypropylamine, aniline, ortho and para toluidines, ortho and para aminophenols, p-anisidine, p-dimethylaminoaniline, o- and p-chloro anilines, p-acetamidoaniline, benzylamine, o-mercaptoaniline, m-aminophenyltrimethoxysilane, 2-aminopyridine, 5- amino-2-mercaptobenzothiazole, cyclohexylamine, cyclohexylmethylamine, N-methylaniline, 2-naphthylamine, ethylenediamine, diethylene triamine, p-phenylenediamine, oxydianiline, 2-mercaptoethylamine, diphenylketimine, 0-ethylhydroxylamine, allylamine, 3-aminocrotononitrile, piperonylamine, piperazine, piperidine, morpholine, 3-(phenylamino)propyltrimethoxysilane, p-aminodiphenylamine, 3-(n-butylamino)-propyltrimethoxysilane, and the like. The preferred organic primary and secondary amines are the aliphatic and aromatic amines, especially the aromatic amines, such as aniline and p-toluidine, and the like.

It is to be understood that such primary and secondary amine accelerators for said episulfide substituted organosilicon coupling agents are additional ingredients employed to enhance the coupling action of the coupling agent and are not to be confused with other conventional additives, such as amine type antioxidants or amine type catalytic accelerators commonly employed in the production of conventional polymer composites, such as sulfur vulcanized elastomers, even though it may be possible, if desired, to employ the same type of organic amine compound for said various different functions. While the production of the articles of manufacture of this invention have been discussed above, when employed, the organic amine employed as the accelerator for the episulfide substituted organosilicon coupling agents can be added to the polymer composite forming formulation prior to, with or immediately after the addition of the silicon coupling agent while in the case of pretreating the inorganic substrate it is preferred to employ a premixture of the amine accelerator and silicon coupling agent. Moreover, when preparing a polymer composite such as an elastomer the polymer composite forming formulation of polymer, substrate (filler), silicon coupling agent and organic amine accelerator (when used) should be prepared first prior to the addition of the further conventional additives for such composites. In general the best results with regard to improved properties of the finished composite should be obtained when the amount of organic amine accelerator employed for the silicon coupling agent is about stoichiometrically equivalent to the amount of silicon coupling agent employed although higher or lower amounts of the amine can be used if desired.

The following examples are illustrative of the present invention and are not to be regarded as limitative. It is to be understood that all parts, percentages and proportions referred to herein and in the claims are by weight unless otherwise indicated. Tensile modulus is defined as the tensile stress in pounds per square inch of original cross-sectional area necessary to produce a given extension in a composite specimen, usually 300% of the unstressed length.

EXAMPLE 1

Into a 250 cc single neck flask equipped with a magnetic stirrer and reflux condenser having a nitrogen bypass for carrying out the reaction under a nitrogen atmosphere were charged about 23.6 grams of distilled glycidoxypropyl trimethoxysilane,

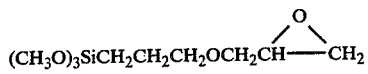

about 8.1 grams of sodium thiocyanate and about 31.7 grams of methanol. The solubilized reaction mixture was stirred at room temperature (about 24° C.) for about 16 hours. The white by-product precipitate of sodium cyanate salt, which slowly formed over said 16 hour period was then filtered out and the methanol solvent stripped off under reduced pressure. The fluid reaction mixture product was then treated with diatomaceous earth and filtered to give the desired fluid 1, 2-epithio-4-oxa-7-trimethoxysilyl heptane product which has the formula

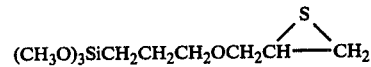

Analysis by infrared absorption spectroscopy and proton magnetic resonance spectroscopy confirmed the above product structure and showed a yield of greater than 98% conversion of the epoxy radical on the starting material to the desired episulfide radical of the product.

EXAMPLE 2

Into a 1-liter, 3-neck flask equipped with a magnetic stirrer, thermometer, and a reflux condenser having a nitrogen by-pass for carrying out the reaction under a nitrogen atmosphere were charged about 269.6 grams of distilled glycidoxypropyltrimethoxysilane, about 86.9 grams of thiourea and about 312.2 grams of methanol. The stirred solubilized reaction mixture was boiled at reflux (about 65° C.) for one hour, then cooled and the methanol solvent stripped out under reduced pressure. The reaction product mixture was then dissolved in diethyl ether and then washed with water to remove the precipitated urea by-product and any unreacted thiourea. The ether solution was then dried with anhydrous magnesium sulfate, filtered, and the ether stripped off under reduced pressure to yield about 234.4 grams of the desired fluid 1, 2-epithio-4-oxa-7-trimethoxysilyl heptane crude product which has the formula

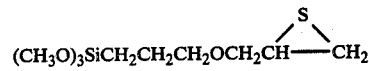

The structure of said crude product was confirmed by infrared absorption spectroscopy, proton magnetic resonance spectroscopy and $C^{13}$ magnetic resonance spectroscopy analysis, as well as by chemical analysis for methoxy and elemental silicon content.

About 40 grams of said crude product were then distilled through a 1-foot Vigreaux column at about 0.18 mm Hg to yield about 35.6 grams of yellowwhite viscous 1,2-epithio-4-oxa-7-trimethoxysilyl heptane oil having boiling points of about 95° C. at 0.07 mm Hg and about 108° C. at 0.18 mm Hg. and a refractive index of $n_D^{20} = 1.460$. The structure for said distilled 1,2-epithio-4-oxa-7-trimethoxysilyl heptane product was confirmed by $C^{13}$ magnetic resonance spectroscopy, laser Raman spectroscopy and vapor phase chromatography.

A further 100 grams of said crude product was distilled in a like manner to give about 90.1 grams of 1,2-epithio-4-oxa-7-trimethoxysilyl heptane having boiling points of about 107° C. at 0.20 mm Hg. and about 110° C. at 0.25mm Hg. and exhibited a purity of about 94.1% by vapor phase chromatographic analysis.

EXAMPLE 3

Into a 500 cc single neck flask equipped with a magnetic stirrer and reflux condenser having a nitrogen by-pass for carrying out the reaction under a nitrogen atmosphere were charged about 24.6 grams of beta-(3,4-epoxycyclohexyl) ethyltrimethoxysilane,

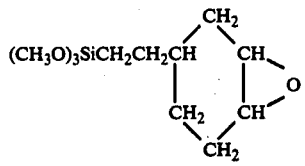

about 7.6 grams of thiourea and about 32.2 grams of methanol. The solubilized reaction mixture was boiled at reflux (about 65° C.) for one hour, then cooled and the methanol solvent stripped out under reduced pressure. The reaction mixture was then dissolved in diethyl ether and washed three times with water to remove the precipitated urea by-product and any unreacted thiourea. The ether solution was then dried with anhydrous magnesium sulfate, filtered, and the ether stripped off under reduced pressure to yield about 23.7 grams of the desired fluid 1,2-epithio-4-(2-trimethoxysilyl) ethyl cyclohexane crude product which has the formula

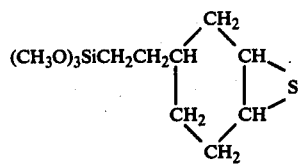

The structure of said crude product was confirmed by infrared absorption spectroscopy and nuclear magnetic resonance spectroscopy analysis, while $C^{13}$ nuclear magnetic resonance spectroscopy analysis showed the crude product to be about 70% pure.

EXAMPLES 4 AND 5

Two vulcanized silica-filled rubber compounds were prepared using the formulations of TABLE I and the same procedure. The silane coupling agent employed in Example 5 was the 1,2-epithio-4-oxa-7-trimethoxysilyl heptane product having a boiling point of about 107° C. at 0.20 mm Hg. of Example 2 above.

TABLE I

| Formulation | Example 4 (Parts by Wt.) | Example 5 (Parts by Wt.) |
|---|---|---|
| Styrene-Butadiene Rubber[1] | 100 | 100 |
| Silica Filler[2] | 35 | 35 |
| Silane Coupling Agent | None | 0.46 |
| Softener Oil[3] | 8.0 | 8.0 |
| BBS[4] | 1.2 | 1.2 |
| DOTG[5] | 2.5 | 2.5 |
| Sulfur | 1.6 | 1.6 |
| Zinc Oxide | 4.0 | 4.0 |
| Stearic Acid | 1.0 | 1.0 |

[1]SBR 1712
[2]Precipitated silica (Hi-Sil 233, Trademark of PPG Industries,Inc.)
[3]Sundex 790, an aromatic processing oil (Trademark of Sun Oil Co.)
[4]N-t-butyl-2-benzothiazole sulfenamide
[5]Di-ortho-tolyl guanidine Each formulation was prepared using a 2 roll rubber mill having a roll temperature of about 130° F. The rubber polymer was charged to the rubber mill and milled until smooth and plastic. Then a small portion of the filler was added to the polymer band, followed by the addition of more filler along with the silane coupling agent (when used) which was added dropwise and concurrently with the filler. After all the silane and about half of the filler had been added the softening oil was added concurrently with the remainder of the filler. After an intimate milled mixture of the styrene-butadiene rubber, silica filler, silane coupling agent (when used), and softener was obtained, the sulfur, accelerators and other ancillary ingredients were added and the mixture further milled until an intimate dispersion was obtained. After storing at ambient room conditions for at least 16 hours, the mixture was remilled until plastic. Molded preformed sheets were cut from the remilled mixture of each formulation and then vulcanized in the same manner in a mold under pressure at 320° F. to 340° F. After resting at ambient room conditions for at least 16 hours the physical properties of the vulcanized molded rubber composites were then measured and the results recorded as shown in TABLE II.

TABLE II

| Properties of Rubber Compounds | Example 4 | Example 5 |
|---|---|---|
| 300% Tensile Modulus (psi)[1] | 353 | 523 |
| Tensile Strength (psi)[1] | 3069 | 3073 |
| Elongation at Break (%)[1] | 760 | 693 |
| Tear Strength (%)[2] | 192 | 227 |

[1]Tested in compliance with ASTM D-412
[2]Tested in compliance with ASTM D-624

The above data demonstrates a significant improvement in the tensile modulus of the silane containing vulcanized rubber compound of Example 5 over the non-silane containing vulcanized rubber compound of control Example 4.

EXAMPLES 6 TO 8

Three vulcanized silica-filled rubber compounds were prepared using the formulations of TABLE III and the same procedure. The silane coupling agent employed in Examples 7 and 8 was the 1,2-epithio-4-oxa-7-trimethoxysilyl heptane product having a boiling point of about 107° C. at 0.20 mm Hg. of Example 2 above.

TABLE III

| Formulation | Example 6 (Parts by Wt.) | Example 7 (Parts by Wt.) | Example 8 (Parts by Wt.) |
|---|---|---|---|
| Styrene-Butadiene Rubber* | 100 | 100 | 100 |
| Silica Filler* | 50 | 50 | 50 |
| Silane Coupling Agent | None | 0.63 | 1.26 |
| Antioxidant A[1] | 1.0 | 1.0 | 1.0 |
| Antioxidant B[2] | 1.0 | 1.0 | 1.0 |
| MBTS[3] | 1.5 | 1.5 | 1.0 |
| DOTG* | 1.5 | 1.5 | 1.0 |
| Sulfur | 2.75 | 2.75 | 2.75 |
| Zinc Oxide | 4.0 | 4.0 | 4.0 |
| Stearic Acid | 1.0 | 1.0 | 1.0 |

*Same as defined in Table I
[1]Flexamine G, a mixture containing about 65% of a complex diarylamine ketone reaction product and about 35% of N,N-diphenyl-p-phenylene diamine (Trademark of United States Rubber Co.)
[2]Phenyl-beta-naphthylamine
[3]2,2'-Benzothiazyl disulfide Each formulation was prepared in the same manner as described in Examples 4 and 5 (the antioxidants, sulfur, accelerators and other ancillary ingredients being added to the mixture after all of the filler and silane coupling agent (when used) had been added), as were the vulcanized rubber composites thereof. The physical properties of said vulcanized rubber products are given in TABLE IV.

TABLE IV

| Properties of Rubber Compounds | Example 6 | Example 7 | Example 8 |
|---|---|---|---|
| 300% Tensile Modulus (psi)* | 1060 | 1390 | 1600 |
| Tensile Strength (psi)* | 2580 | 2790 | 2810 |
| Elongation at Break (%)* | 475 | 450 | 425 |
| Tear Strength (psi)* | 295 | 280 | 330 |

*Same as defined in TABLE II

The above data demonstrates a significant improvement in the tensile modulus of the silane containing vulcanized rubber compounds of Examples 7 and 8 over the non-silane containing vulcanized rubber compound of control Example 6.

EXAMPLES 9 AND 10

Two vulcanized silica-filled rubber compounds were prepared using the formulations of TABLE V and the same procedure. The silane coupling agent employed in Example 10 was the 1,2-epithio-4-oxa-7-trimethoxysilyl heptane product having a boiling point of about 107° C. at 0.20 mm Hg. of Example 2 above.

TABLE V

| Formulation | Example 9 (Parts by Wt.) | Example 10 (Parts by Wt.) |
|---|---|---|
| Styrene-Butadiene Rubber* | 100 | 100 |
| Silica Filler* | 35 | 35 |
| Silane Coupling Agent | None | 0.88 |
| Softener Oil* | 8.0 | 8.0 |
| ZMDC** | 0.75 | 0.75 |
| Sulfur | 2.0 | 2.0 |
| Zinc Oxide | 5.0 | 5.0 |
| Stearic Acid | 1.0 | 1.0 |

*Same as defined in TABLE I
**Zinc dimethyl dithiocarbamate

Each formulation was prepared in the same manner as described in Examples 4 and 5, as were the vulcanized molded rubber product composites thereof. The physical properties of said vulcanized molded rubber products are given in TABLE VI.

TABLE VI

| Properties of Rubber Compounds | Example 9 | Example 10 |
|---|---|---|
| 300% Tensile Modulus (psi)* | 59 | 259 |
| Tensile Strength (psi)* | 760 | 1776 |
| Elongation at Break (%)* | 1100 | 867 |
| Tear Strength (psi)* | 147 | 182 |

*Same as defined in TABLE II.

The above data demonstrates a significant improvement in the tensile modulus and tear strength of the silane containing vulcanized rubber compound of Example 10 over the non-silane containing vulcanized rubber compound of control Example 9.

EXAMPLES 11 TO 14

Four vulcanized silica-filled rubber compounds were prepared using the formulations of TABLE VII and the same procedure. The silane coupling agent employed in Examples 12 and 14 was the 1,2-epithio-4-oxa-7-trimethoxysilyl heptane product having a boiling point of about 107° C. at 0.20 mm Hg. of Example 2 above.

TABLE VII

| Formulation | Ex.11 (Parts by Wt.) | Ex.12 (Parts by wt.) | Ex.13 (Parts by Wt.) | Ex. 14 (Parts by Wt.) |
|---|---|---|---|---|
| Styrene-Butadiene Rubber* | 100 | 100 | 100 | 100 |
| Silica Filler* | 35 | 35 | 35 | 35 |
| Silane Coupling Agent* | None | 0.88 | None | 0.88 |
| Aniline | 0.325 | 0.325 | None | None |
| Piperidine | None | None | 0.30 | 0.30 |
| Softener Oil* | 8.0 | 8.0 | 8.0 | 8.0 |
| ZMDC** | 0.75 | 0.75 | 0.75 | 0.75 |
| Sulfur | 2.0 | 2.0 | 2.0 | 2.0 |
| Zinc Oxide | 5.0 | 5.0 | 5.0 | 5.0 |
| Stearic Acid | 1.0 | 1.0 | 1.0 | 1.0 |

*Same as defined in TABLE I
**Same as defined in TABLE V

Each formulation was prepared in the same manner as described in Examples 4 and 5, the aniline and piperidine (when used) being added concurrently with a portion of the filler and subsequent to the addition of any silane, as were the vulcanized molded rubber product composites thereof. The physical properties of said vulcanized molded rubber products are given in TABLE VIII.

TABLE VIII

| Properties of Rubber Compounds | Ex. 11 | Ex. 12 | Ex. 13 | Ex. 14 |
|---|---|---|---|---|
| 300% Tensile Modulus (psi)* | 138 | 270 | 191 | 511 |
| Tensile Strength (psi)* | 1077 | 1932 | 1351 | 2499 |
| Elongation at Break (%)* | 1017 | 790 | 840 | 673 |
| Tear Strength (psi)* | 137 | 192 | 138 | 250 |

*Same as defined in TABLE II

The above data demonstrates a significant improvement in the tensile modulus of the silane and amine containing vulcanized rubber compounds of Examples 12 and 14 over the amine containing but silane-free vulcanized rubber compounds of control Examples 11 and 13 as well as over the silane containing vulcanized rubber compound of Example 10.

EXAMPLE 15

This example illustrates the production of a homopolymeric episulfide substituted organosiloxane by hydrolyzing and condensing an episulfide substituted organosilane.

About 1.0 grams of the distilled 1,2-epithio-4-oxa-7-trimethoxysilyl heptane product having a boiling point of about 107° C. at 0.20 mm Hg. of Example 2 above, along with about 5.0 grams of methanol and about 1.0 grams of glacial acetic acid was added to a 50 cc beaker. Water was then slowly added until the aqueous mixture became hazy. The mixture was then stirred until clear. Another increment of water was added until the mixture was hazy. The mixture was again stirred until it cleared. This procedure was repeated until about 20.0 grams of water had been added. Hydrolysis and condensation to a homopolymeric siloxane formation having the siloxy unit

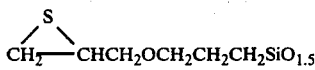
CH₂——CHCH₂OCH₂CH₂CH₂SiO₁.₅ was confirmed by Raman spectroscopy, proton magnetic resonance spectroscopy, and by titration for the cyclic episulfide noiety. The siloxane concentration product was found to be stable, i.e. no gel or precipitate formation, for more than 24 hours.

EXAMPLE 16

This example illustrates the production of a thermoset resin-glass fabric laminate article of manufacture.

A 0.1% by weight aqueous 1,2-epithio-4-oxa-7-trimethoxysilyl heptane solution of Example 15 was used to treat a twelve 7 inch wide woven glass fabric strip by dipping the glass trips into the solution. The treated woven glass fabric was then hung dry at ambient temperature for 20 minutes and then dried in a forced air oven at 135° C. for about 2 to 3 minutes. The dried treated glass fabric was then cut into 12 inch squares and used to prepare a dry sandwich laminate by alternating twelve plies off treated glass fabric and eleven plies of a thermoset resin which was prepared by mixing 300.0 parts by weight of an epoxide resin and 45.0 parts by weight of meta-phenylene diamine. The laminate was then pressed to stops in a pre-heated press for 30 minutes at 250° C. and post cured in a forced air oven at 200° C. for one hour.

The laminate was then cut into ten 4 × ½ inch test specimens and tested for flexural strength both initially and after immersion in boiling water after 72 hours, according to ASTM Specification D-790 using a Baldwin-Tate Tester.

The test specimens showed an initial flexural dry strength of 64,606 psi and a flexural wet strength of 53,780 after 72 hours in boiling water. In addition, the test specimens showed a percent wet retention (i.e. flexural wet strength, psi, divided by flexural dry strength, psi times 100) of 83.2 and a % water pickup (i.e. wet weight of specimen minus dry weight of specimen divided by dry weight of specimen times 100) of 1.06. By comparison, a glass laminate prepared in the same manner but from unfinished glass fabric had an initial flexural dry strength of 56,643, a flexural wet strength of 31,090, a % wet retention of 54.9 and a % water pick-up of 1.52.

EXAMPLE 17

This example illustrates the pretreatment of a silica filler with an episulfide substituted organosilicon coupling agent.

One thousand parts by weight of a silica filler (Hi-Si 233) was dried at 80° C. for 18 hours and cooled to room temperature. About 16.4 parts by weight of the 1,2-epithio-4-oxa-7-trimethoxysilyl heptane product having a boiling point of about 107° C. at 0.2 mm Hg. of Example 2 above was mixed with about 150 parts of weight of a 90/10 (methanol/water) solvent and stirred for 20 minutes. The aqueous mixture was charged into a large dropping funnel attached to a twin shell blender. About 650 parts by weight of the dried silica filler was then added at a steady rate and the total blend mixed for 20 minutes. The wet silica treated mixture was then charged to a large pan and dried for 18 hours at 80° C. After drying about 71.8 grams of the episulfide silicon treated silica filler was obtained.

EXAMPLES 18 to 20

Three vulcanized silica-filler rubber compounds were prepared using the formulations in TABLE IX and the same procedure. The silicon coupling agent employed in Example 19 was the 1,2-epithio-4-oxa-7-trimethoxysilyl heptane product having a boiling point of about 107° C. at 0.20 mm Hg. of Example 2 above, while the silica filler and silicon coupling agent employed in Example 20 was the episulfide substituted organosilicon pretreated silica filler product of Example 17.

TABLE IX

| Formulation | Ex.18 (Parts by Wt.) | Ex. 19 (Parts by Wt.) | Ex. 20 (Parts by Wt.) |
|---|---|---|---|
| Styrene-Butadiene Rubber* | 100 | 100 | 100 |
| Silica Filler* | 35 | 35 | AS** |
| Silicon Coupling Agent | None | 1.8 | Described** |
| Softener Oil* | 8.0 | 8.0 | 8.0 |
| BBS* | 1.2 | 1.2 | 1.2 |
| DOTG* | 2.5 | 2.5 | 2.5 |
| Sulfur | 1.6 | 1.6 | 1.6 |
| Zinc Oxide | 4.0 | 4.0 | 4.0 |
| Stearic Acid | 1.0 | 1.0 | 1.0 |

*Same as defined in Table I
**35.9 parts by weight of the episulfide substituted organosilicon pretreated silica filler product of Example 17

Each formulation was prepared in the same manner as described in Examples 4 and 5, as were the vulcanized rubber composites thereof. The physical properties of said vulcanized rubber products are given in Table X.

TABLE X

| Properties of Rubber Compounds | Example 18 | Example 19 | Example 20 |
|---|---|---|---|
| 300% Tensile Modulus (psi)* | 234 | 483 | 496 |
| Tensile Strength (psi)* | 2906 | 2884 | 3654 |
| Elongation at Break (%)* | 840 | 742 | 777 |
| Tear Strength (psi)* | 153 | 231 | 238 |

*Same as defined in TABLE II

The above data demonstrates a significant improvement in the tensile modulus of the silicon containing vulcanized rubber compound, regardless of whether the silicon was employed as a neat silane (Example 19) or in the form of a silicon pretreated filler (Example 20) over the non-silicon containing vulcanized rubber compound of control Example 18.

EXAMPLE 21

This example illustrates the production of a homopolymeric episulfide substituted organosiloxane by hydrolyzing and condensing an episulfide substituted organosilane.

About 6.3 grams of the distilled 1,2-epithio-4-oxa-7-trimethoxysilyl heptane product having a boiling point of about 107° C. at 0.20 mm Hg. of Example 2 above and about 0.45 grams of water were charged to a 100 ml flask and stirred until homogeneous. The flask was then stoppered tightly and allowed to stand at ambient temperature for two weeks. Hydrolysis and condensation of the silane monomer to a homopolymeric siloxane formation having the siloxy unit,

in the aqueous solution was followed and confirmed by infrared spectroscopy analysis. Retention of the episulfide moiety on the siloxane product in the aqueous solution was also confirmed by proton magnetic resonsance spectroscopy analysis.

EXAMPLE 22

This example illustrates the production of a copolymeric episulfide substituted organosiloxane by hydrolyzing and condensing an episulfide substituted organosilane and another silane monomer.

About 10.0 grams of the distilled 1,2-epithio-4-oxa-7-trimethoxysilyl heptane product having a boiling point of about 107° C. at 0.20 mm Hg. of Example 2 above were charged to a 100 ml. flask followed by about 5.4 grams of methyltrimethoxysilane, $CH_3Si(OCH_3)_3$, about 2.2 grams of water and about 8.0 grams of methanol. The mixture was stirred until homogeneous and allowed to stand at ambient temperature for two weeks. Hydrolysis and condensation of the two silane monomers to a copolymeric siloxane formation having the siloxy units

and $CH_3SiO_{1.5}$ in the aqueous solution was followed and confirmed by infrared spectroscopy analysis.

EXAMPLES 23 to 26

Four vulcanized silica-filler rubber compounds were prepared using the formulations in TABLE XI and the same procedure. The silicon coupling agent employed in Example 24 was the 1,2-epithio-4-oxa-7-trimethoxysilyl heptane product having a boiling point of about 107° C. at 0.20 mm Hg. of Example 2 above. The silicon coupling agent employed in Example 25 was the aqueous episulfide substituted organosilicon solution product of Example 21. The silicon coupling agent employed in Example 26 was the aqueous-methanol episulfide substituted organosilicon solution product of Example 22.

TABLE XI

| Formulation | Ex. 23 (Parts by Wt.) | Ex. 24 (Parts by Wt.) | Ex. 25 (Parts by Wt.) | Ex. 26 (Parts by Wt.) |
| --- | --- | --- | --- | --- |
| Styrene-Butadiene Rubber* | 100 | 100 | 100 | 100 |
| Silica Filler* | 35 | 35 | 35 | 35 |
| Silicon Coupling Agent | None | 1.8 | 2.02 | 4.24 |
| Softener Oil* | 8.0 | 8.0 | 8.0 | 8.0 |
| BBS* | 1.2 | 1.2 | 1.2 | 1.2 |
| DOTG* | 2.5 | 2.5 | 2.5 | 2.5 |
| Sulfur | 1.6 | 1.6 | 1.6 | 1.6 |
| Zinc Oxide | 4.0 | 4.0 | 4.0 | 4.0 |
| Stearic Acid | 1.0 | 1.0 | 1.0 | 1.0 |

*Same as defined in Table I

Each formulation was prepared in the same manner as described in Examples 4 and 5, as were the vulcanized rubber composites thereof. The physical properties of said vulcanized rubber products are given in Table XII.

TABLE XII

| Properties of Rubber Compounds | Example 23 | Example 24 | Example 25 | Example 26 |
| --- | --- | --- | --- | --- |
| 300% Tensile Modulus (psi)* | 234 | 483 | 453 | 481 |
| Tensile Strength (psi)* | 2906 | 2884 | 3415 | 3558 |
| Elongation at Break (%)* | 840 | 742 | 797 | 775 |
| Tear Strength (psi)* | 153 | 231 | 242 | 251 |

*Same as defined in TABLE II

The above data demonstrates a significant improvement in the tensile modulus of the silicon containing vulcanized rubber compounds of Examples 24 to 26 over the non-silicon containing vulcanized rubber compound of control Example 23.

As noted above, the episulfide substituted organosilicon compositions of matter are extremely effective coupling agents and thus offer exceptional promise in the production of filled-vulcanized rubber articles such as tires, gaskets, hoses, and other conventional mechanical rubber goods.

Various modifications and variations of this invention will be obvious to a worker skilled in the art and it is to be understood that such modifications and variations are to be included within the purview of this application and the spirit and scope of the appended claims.

What is claimed is:

1. A polymer composite article of manufacture comprising the reaction product of a composition comprising (a) an organic polymer selected from the class consisting of thermoplastic forming resins and thermoset forming resins, (b) a siliceous reinforcing material and (c) an episulfide substituted organosilane coupling agent having the formula

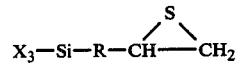

wherein X is a methoxy or ethoxy radical and R is a propyleneoxymethylene radical.

2. A thermoplastic resin article of manufacture as defined in claim 1, wherein the organic polymer is a thermoplastic forming resin.

3. A thermoset resin article of manufacture as defined in claim 1, wherein the organic polymer is a thermoset forming resin.

4. A polymer composite article of manufacture comprising the reaction product of a composition comprising (a) vulcanizable styrene-butadiene rubber, (b) precipitated silica, (c) aniline and (d) 1,2-epithio-4-oxa-7-trimethoxysilyl heptane.

5. A polymer composite article of manufacture comprising the reaction product of a composition comprising (a) vulcanizable styrene-butadiene rubber, (b) precipitated silica, (c) piperidine and (d) 1,2-epithio-4-oxa-7-trimethoxysilyl heptane.

* * * * *

UNITED STATES PATENT AND TRADEMARK OFFICE
CERTIFICATE OF CORRECTION

PATENT NO. : 4,140,830
DATED : February 20, 1979
INVENTOR(S) : Thomas C. Williams and George E. Totten It is certified that error appears in the above-identified patent and that said Letters Patent are hereby corrected as shown below:

Col. 1, line 35, after "abandoned" insert ---.---.

Col. 1, line 66, change "atoms" to read --atom---.

Col. 2, line 17, change "provisor" to read ---proviso---.

Col. 6, line 62 change "matal" to read ---metal---.

Col. 8, line 24, that portion of the formula shown as "$-\overset{\diagup \diagdown}{CH}-CH_2$" should read -- $-\overset{\diagup S \diagdown}{CH}-CH_2$ ---.

Col. 21, line 59, "parts of weight" should read ---parts by weight---.

Col. 22, line 49 change "compound" to ---compounds---.

Signed and Sealed this

Eleventh Day of December 1979

[SEAL]

Attest:

SIDNEY A. DIAMOND

Attesting Officer  *Commissioner of Patents and Trademarks*